(12) United States Patent
Miller et al.

(10) Patent No.: US 6,969,608 B1
(45) Date of Patent: Nov. 29, 2005

(54) PHARMACEUTICALS CONTAINING MULTIPOTENTIAL PRECURSOR CELLS FROM TISSUES CONTAINING SENSORY RECEPTORS

(75) Inventors: Freda Miller, Montreal (CA); Andrew Gloster, Saskatoon (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 08/920,272

(22) Filed: Aug. 22, 1997

Related U.S. Application Data

(60) Provisional application No. 60/024,590, filed on Aug. 26, 1996, provisional application No. 60/024,456, filed on Aug. 27, 1996.

(51) Int. Cl.[7] .................................................. C12N 5/00
(52) U.S. Cl. ...................... 435/325; 435/368; 435/352; 435/353; 435/354; 424/93.1; 424/93.7
(58) Field of Search ............................... 435/368, 325, 435/353, 354; 424/93.1, 93.7

(56) References Cited

U.S. PATENT DOCUMENTS

| | | | | |
|---|---|---|---|---|
| 5,318,907 A | * | 6/1994 | Ronnette et al. | ....... 435/240.21 |
| 5,338,839 A | | 8/1994 | McKay et al. | |
| 5,753,506 A | | 5/1998 | Johe | |
| 5,824,489 A | * | 10/1998 | Anderson et al. | .......... 435/7.21 |
| 5,912,175 A | | 6/1999 | Wille, Jr. | |
| 6,001,654 A | | 12/1999 | Anderson et al. | |

FOREIGN PATENT DOCUMENTS

| | | | |
|---|---|---|---|
| WO | 93/01275 | 1/1993 | ............ C12N 5/00 |
| WO | 94/09119 | 4/1994 | ............ C12N 5/08 |
| WO | 94/10292 | 5/1994 | ............ C12N 5/06 |
| WO | 94/16718 | 8/1994 | ............ A61K 37/00 |
| WO | WO 9416718 A | 8/1994 | |
| WO | 95/13364 | 5/1995 | ............ C12N 5/06 |
| WO | WO 9512665 A | 5/1995 | |
| WO | WO 9741208 A | 11/1997 | |
| WO | WO 9956759 A | 11/1999 | |

OTHER PUBLICATIONS

Calof et al., Neuron, 3, 315, Jul. 1989.*
Mayo et al., Int. J. Dev. Biol. 36, 255, 1992.*
Fraichard A, et al. In vitro differentiation of embryonic stem cells and functional neurons. Journal of Cell Science 108, 3181-3185 (1995).*
Kaufman SJ, Replicating myoblasts express a muscle-specific phenotype. Proc. Natl. Acad. Sci. USA vol. 85, pp. 9606-9610, Dec. 1988.*
La Salle G. An Adenovirus vector for Gene Transfer into Neurons and Glia in the brain. Science, vol. 259, pp. 988-990 (1993).*
Mayo ML, Desmin expression during early mouse tongue morphogenesis. Int. J. Dev. Biol. 36:255-263 (1992).*

Schubert D, Ontogeny of electrically excitable cells in cultured olfactory epithelium. Proc. Natl. Acad. Sic. USA, vol. 82, pp. 7782-7786, Nov. 1985.*
Sosnowski JS, Chemical traumatization of adult mouse olfactory epithelium in situ stimulates growth and differentiation of olfactory neurons in vitro. Brain Res. Dec. 8, 1195;702(1-2):37-48.*
Avoli et al. Pharmacology and Electrophysiology of a synchronous GABA-Mediated Potential in the Human Neocortex. Neuroscience vol. 62 No. 3, pp. 655-666, 1994.*
Bruckenstein et al. Morphological Differentiation of Embryonic Rat Sympathetic Neurons in Tissue Culture. Developmental Biology vol. 128 pp. 324-336, 1988.*
Burns S. et al., (1983) "A primate model of parkinsonism: selective destruction of dopaminergic neurons in pars compacta of the substantia nigra by N-methyl-4-phenyl-1, 2,3,6-tetra-hydropyridine." Proc Natl Acad Sci (USA) 80: 4546-4550.
Fahn S. (1992) "Fetal-tissue transplants in Parkinson'disease." New England Journal of Medicine. 327: 1589-1590.
Dunnett SB. et al., (1991) "Nigral transplants in primate models of parkinsonism.". In: Lindvall O., Bjorkland A., Widner H., eds. Intracerebral transplantation in movement disorders. Restorative Neurology 4:27-51.
Langston JW. et al., (1983) "Chronic parkinsonism in humans due to a product of meperidine analog synthesis." Science 219:979-980.
Widner H. et al., (1993) "Bilateral fetal mesencephalic grafting in two patients with parkinsonism induced by 1-methyl-4-phenyl-1,2,3,6-tetrahydropyridine (MPTP)." New England Journal of Medicine 327:1556-1563.
Winkler C. et al., (1995) "EGF-responsive neural progenitor cells, survive, migrate and differentiate after transplantation into the adult rat striatum." Society for Neuroscience Abstracts 21:2029.

(Continued)

Primary Examiner—Joseph Murphy
(74) Attorney, Agent, or Firm—Clark & Elbing LLP; Kristina Bieker-Brady

(57) ABSTRACT

Current sources of neural stem and progenitor cells for neural transplantation are essentially inaccessible in living animals. This invention relates to neural precursor cells (stem cells, progenitor cells or a combination of both types of cells) isolated from the olfactory epithelium of mammals that can be passaged and expanded, and that will differentiate into cell types of the central nervous system (CNS), including astrocytes, oligodendrocytes, and tyrosine-hydroxylase-positive neurons. These precursor cells provide an accessible source for autologous transplantation in CNS, PNS, spinal cord and other damaged tissues.

11 Claims, 10 Drawing Sheets

OTHER PUBLICATIONS

Gage FH. et al., (1995) "Survival and differentiation of adult neuronal progenitor cells transplanted to the adult brain." Proc Natl Acad Sci (USA) 92:11870-11883.

Reynolds B. and Weiss S., (1992) Science 255:107.

Weiss S. et al., (1996) "Is there a neural stem cell in the mammalian forebrain?" T.I.N.S. 19:9:1.

Peel AL. et al., (1995) "Co-localization of glial and neuronal markers in EGF-generated cultures of pluripotent CNS stem cells." Society for Neuroscience Abstract 21:285.

Ruth S. Slack et al., (1996) "Adenovirus-mediated Gene Transfer of the Tumor Supressor, p53, Induces Apoptosis in Postmitotic Neurons." The Journal of Cell Biology, vol. 135, No. 4 1085-1096.

Le Gal La Salle et al., (1993) "An adenovirus vector for gene transfer into neurons and glia in the brain." Science, 259: 988-990.

R.S. Slack et al., (1996) "Viral vectors for use in modulating gene expression in neurons", Curr. Opin. Neurobiot, 6:576-583.

I. Lefkowitz et al., "Limiting Dilution Analysis of Cells in the Immune System." Cambridge University Press, Cambridge, U.K. (1979).

C. G. Bellows et al., Dev. Biol. 133, 8 (1989).

A. Carlsson et al., Nature 180, 1200 (1957).

U. Ungerstedt et al., Brain Res. 24, 485 (1970).

A. Gloster et al., J. Neurosci, 14, 7319 (1994).

S. Bamji et al. Comp. Neurol. 374, 52 (1996).

E. Soriano et al., J. Histochem. Cytochem. 39, 255 (1991).

Ehringer, H. et al., "Verteilung von noradrenalin und dopamin (3-hydroxytyramin) im gehirn des menschen und ihr verhalten bei erkrankungen des extrapyramidalen systems", Kllin. Wschr. 38: 1236-1239 (1960).

Ourendnik et al., "Neural stem cells- a versatile tool for cell replacement and gene therapy in the central nervous system", Clin. Genet. 56:267-278 (1999).

* cited by examiner

# PHARMACEUTICALS CONTAINING MULTIPOTENTIAL PRECURSOR CELLS FROM TISSUES CONTAINING SENSORY RECEPTORS

CROSS REFERENCE TO RELATED APPLICATIONS

This application claims the benefit of U.S. Provisional Application No. 60/024,590, filed Aug. 26, 1996, and U.S. Provisional Application No. 60/024,456 filed Aug. 27, 1996 which are incorporated by reference herein in their entirety.

FIELD OF THE INVENTION

The present invention relates to multipotential precursor cells isolated from peripheral tissues containing sensory receptors such as the olfactory epithelium and tongue. The invention also relates to cells differentiated from the precursor cells. The invention includes pharmaceutical compositions containing precursor cells. The invention also includes cells differentiated from precursor cells and uses for those cells.

BACKGROUND OF THE INVENTION

There are a number of diseases of the central nervous system ("CNS") which have a devastating effect on patients. These diseases are incurable and debilitating. They include Alzheimer's disease, Huntington's disease, Parkinson's disease and Multiple Sclerosis, to name a few.

By way of example, Parkinson's disease is a progressive degenerative disorder of unknown cause. In healthy brain tissue, dopaminergic neurons extend from the substantia nigra of the brain into the striatum. Parkinson's disease occurs when these dopaminergic neurons die. There are a number of methods to treat Parkinson's disease.

One method is to treat humans having parkinsonism with L-DOPA. Another method is to transplant cells into the substantia nigra or striatum. Transplanted cells replace endogenous cells that are lost as a consequence of damage. Transplanted cells may also be used as vectors for the expression of therapeutic molecules. Another method is to implant fetal brain grafts containing dopaminergic neurons. This method is experimental (Widner et al., 1993; Callahan et al., 1992). An animal model of Parkinson's disease is an MPTP-treated non-human primate. The animal models have been transplanted with dopamine-rich embryonic neurons with some success (Dunnett et al., 1991). (MPTP is a selective dopaminergic toxicant that produces parkinsonian symptoms in humans and in primates after a one-hit lesion to the neurons in the substantia nigra (Langston et al., 1983; Burns et al., 1983)).

Investigators studying other neurodegenerative diseases, such as Alzheimer's disease and Huntington's disease, are exploring the possible usefulness of fetal-tissue implants in the treatment of these diseases.

Current approaches to transplantation suffer from a number of serious limitations. First, many investigators are utilizing non-neural cells such as fibroblasts or transformed cell lines for transplantation. Second, the safety of transplantation of immortalized cell sources into the human brain is a concern. These cells may become unregulated and develop into tumors. Third, transplants of dopaminergic neuron fetal tissue to Parkinson's disease patients have a number of difficulties:

the fate of implanted dopaminergic neurons in patients with Parkinson's disease is uncertain—whatever caused the loss of endogenous dopaminergic neurons may also eventually injure the implanted ones, in many cases, implants provide only temporary relief as the symptoms associated with the disease often return after a number of years, the patient may reject foreign fetal tissue, there are adverse reactions associated with immunosuppression (immunosuppression is needed to try to help the patient accept the foreign fetal tissue, even though the brain is, to some degree, immunologically privileged), a sufficient number of cells in the fetal tissue being implanted are unable to survive during and after implantation, the implants may not be regulated by the host brain, other diseases or disorders may be transmitted to the patient via the implant, the cost and effort associated with implanting fetal tissue may not be justified by the results, and there are objections to the ethics associated with implanting fetal tissue.

Many of these problems are encountered with transplants used to treat other neurodegenerative diseases, disorders or abnormal physical states.

In some tissues, stem cells and progenitor cells are proposed as a source for alternative treatments of disease or injury to tissues. The proposed treatments involve transplants of healthy tissue or endogenous stimulation of stem cells or progenitor cells to produce healthy tissue.

Stem cells are undifferentiated cells that exist in many tissues of embryos and adult mammals. In embryos, blastocyst stem cells are the source of cells which differentiate to form the specialised tissues and organs of the developing fetus. In adults, specialised stem cells in individual tissues are the source of new cells which replace cells lost through cell death due to natural attrition, disease or injury. No stem cell is common to all tissues in adults. Rather, the term "stem cell" in adults describes different groups of cells in different tissues and organs with common characteristics.

Stem cells are capable of producing either new stem cells or cells called progenitor cells. A progenitor cell differentiates to produce the mature specialized cells of mammalian organs. In contrast, stem cells never terminally differentiate (i.e. they never differentiate into specialized tissue cells). Progenitor cells and stem cells are referred to collectively as "precursor cells". This term is often used when it is unclear whether a researcher is dealing with stem cells or progenitor cells or a combination of both cells.

Progenitor cells may differentiate in a manner which is unipotential or multipotential. A unipotential progenitor cell is one which can form only one particular type of cell when it is terminally differentiated. A multipotential progenitor cell has the potential to differentiate to form more than one type of tissue cell. Which type of cell it ultimately becomes depends on conditions in the local environment such as the presence or absence of particular peptide growth factors, cell—cell communication, amino acids and steroids. For example, it has been determined that the hematopoietic stem cells of the bone marrow produce all of the mature lymphocytes and erythrocytes present in fetuses and adult mammals. There are several well-studied progenitor cells produced by these stem cells, including three unipotential and one multipotential tissue cell. The multipotential progenitor cell may divide to form one of several types of differentiated cells depending on circumstances such as which hormones or factors act upon it and cell—cell contact.

Weiss et al, 1996, summarises the five defining characteristics of stem cells as the ability to:

Proliferate: Stem cells are capable of dividing to produce daughter cells.

Exhibit self-maintenance or renewal over the lifetime of the organism: Stem cells are capable of reproducing by dividing symmetrically or asymmetrically to produce new stem cells. Symmetric division occurs where one stem cell divides into two daughter stem cells. Asymmetric division occurs where one stem cell forms one new stem cell and one progenitor cell. Symmetric division is a source of renewal of stem cells. This permits stem cells to maintain a consistent level of stem cells in an embryo or adult mammal.

Generate large number of progeny: Stem cells may produce a large number of progeny through the transient amplification of a population of progenitor cells.

Retain their multilineage potential over time: Stem cells are the ultimate source of differentiated tissue cells, so they retain their ability to produce multiple types of progenitor cells, which will in turn develop into specialized tissue cells.

Generate new cells in response to injury or disease: This is essential in tissues which have a high turnover rate or which are more likely to be subject to injury or disease, such as the epithelium or blood cells.

Thus, the key features of stem cells are that they are multipotential cells which are capable of long-term self-renewal over the lifetime of a mammal.

There has been much effort to isolate stem cells and determine which peptide growth factors, hormones and other metabolites influence stem cell renewal and production of progenitor cells, which conditions control and influence the differentiation of progenitor cells into specialized tissue cells, and which conditions cause a multipotential progenitor cell to develop into a particular type of cell.

Stem cells or progenitor cells may be used as substrates for producing healthy tissue where a disease, disorder or abnormal physical state has destroyed or damaged normal tissue. For example, stem cells and progenitor cells may be used as a target for in vivo stimulation with growth factors or they may be used as a source of cells for transplantation. The stem cells or progenitor cells may be transplanted or they may be induced to produce healthy differentiated cells for transplant.

In several tissues, stem cells have been isolated and characterised in an attempt to develop new therapies to repair or replace damaged tissues. For example, neural stem cells have been isolated from the mammalian brain (Reynolds and Weiss, Science 255:107 (1992)) and these cells were shown to be multipotential and able to differentiate into neurons, astrocytes and oligodendrocytes. WO 93/01275, WO 94/16718, WO 94/10292 and WO 94/09119 describe uses for these cells.

WO 95/13364 reports the delivery of growth factors to the ventricles of the CNS in order to stimulate neural stem cells to proliferate and produce neural progenitor cells which will develop into neurons, oligodendrocytes or astrocytes. This procedure has many complications which must be addressed before it may be used clinically. Differentiating the target neural stem cells or neural progenitor cells into a desired type of tissue which is functional is one complication. Another complication is choosing a growth factor which does not cause side effects in other areas of the brain.

These publications are limited to isolating or using adult stem cells from the brain (in particular, the tissue around the brain ventricles, the ventricle ependyma, which is the remnant of the embryonic brain germinal zone). Although these publications suggest that progenitor cells may be isolated from the adult peripheral nervous system ("PNS"), the publications define the PNS as the system which originates from the neural crest. There is no reported isolation of a stem cell from the PNS which does not originate from the neural crest.

There are no clinical treatments involving transplants of neural stem cells or neural progenitor cells isolated from the brain nor are there clinical treatments using differentiated cells produced from the neural stem cells or neural progenitor stem cells isolated from the brain. There are also no clinical treatments to endogenously stimulate the neural stem cells or neural progenitor cells of the brain in vivo to produce differentiated cells. Even if there were clinical procedures to transplant fetal neural stem cells or neural progenitor cells from the brain, or to transplant cells differentiated from these stem cells or progenitor cells (e.g. dopaminergic neurons into Parkinson's disease patients), this would not overcome the many problems of transplants from one human to another. As mentioned above, the only current, accessible human source for these neural stem cells and neural progenitor cells is aborted human fetuses, raising serious ethical concerns. Heterologous transplants are also very risky and complicated because of problems with graft rejection, immunosuppression, and the potential for donor grafts transferring diseases or disorders to a recipient. Encapsulation of cells in microspheres has the potential to decrease the likelihood of graft rejection, but this effect is lost if the integrity of the microsphere is disrupted. There is a clear need for safer tissue grafts which can be transplanted to a recipient without being rejected.

The safest type of tissue graft would be one that comes from self (an autologous tissue source). Autologous tissue sources are widely used in procedures such as bone transplants and skin transplants because a source of healthy tissue is readily accessible for transplant to a damaged tissue site. In brain diseases, such as Parkinson's disease, healthy dopaminergic neuronal brain tissue may exist at other sites in the brain but attempts to transplant these neurons would harm the site where the healthy neurons originate. Neural stem cells or neural precursor cells that can be differentiated into dopaminergic neurons may be available at the damaged site or at other sites from which they may be transplanted, but the CNS, particularly the brain, is physically difficult to access. It would be impractical or impossible to access brain or other CNS tissue for biopsy and then again for transplant in patients with weakened health. It would be very useful if there were accessible stem cells or progenitor cells that could be differentiated into CNS cell types, such as dopaminergic neurons, to provide a source of cells for autologous transplants.

It would be useful if neural stem cells or progenitor cells could be identified and isolated outside the CNS and outside the PNS which originates from the neural crest. Medical treatments could then be developed using those neural stem cells, neural progenitor cells or cells differentiated from those cells. It is clear that despite the work that has been done to attempt to treat neurodegenerative diseases by tissue transplant, a need still exists for a pharmaceutical composition in which (1) the composition is accepted by the patient, thus avoiding the difficulties associated with immunosuppression, (2) the composition is safe and effective, thus justifying the cost and effort associated with treatment, (3)

the composition provides long term relief of the symptoms associated with the disease, (4) the composition is efficacious during and after transplantation and (5) there are no objections to the ethics of the composition's use.

Thus, there is a clear need to develop neural stem cell cultures or neural progenitor cell cultures from accessible tissues of the PNS which can act as a source of cells that are transplantable to the CNS, PNS, spinal cord or other tissues in vivo in order to replace damaged tissue.

SUMMARY OF THE INVENTION

This invention relates to the isolation of "precursor cells" (which may be neural stem cells or neural progenitor cells or a combination of both types of cells) from peripheral tissue with sensory receptors, specifically olfactory epithelium and tongue, of the PNS. The olfactory epithelium is part of the PNS, but does not originate from the neural crest. Rather, it is of placodal origin. Hence, peripheral sensory neurons of the olfactory epithelium are developmentally distinct from the neurons of the neural crest derived PNS. Olfactory precursor cells have been isolated, determined to be multipotential and capable of generating CNS cell types. Thus, they are a useful source of tissue for autologous or heterologous transplant to the CNS, PNS, spinal cord and other damaged tissues.

The invention also includes isolated and purified precursor cells of a mammal from peripheral tissue containing sensory receptors, wherein the precursor cells are selected from a group consisting of neural stem cells, neural progenitor cells and a combination of neural stems cells and neural progenitor cells. The cells can be isolated from tongue.

The inventors have isolated precursor cells from the olfactory epithelium of mammals (juvenile and adult mice, adult rat and humans). The precursor cells of the olfactory epithelium possess the two key characterising features of stem cells: they are mutipotential and are self-renewing. They can be passaged and differentiated into cell types of the CNS, including astrocytes, oligodendrocytes, and dopaminergic neurons. Precursor cells isolated from the olfactory epithelium of neonatal mice express the immunological marker of neural stem and progenitor cells, nestin. These cells are not restricted to assuming an olfactory phenotype, but instead can differentiate into astrocytes, oligodendrocytes, and dopaminergic neurons. This shows that the olfactory epithelium is a useful source of dopaminergic neurons for homotypic grafts into Parkinson's Disease patients. The precursor cells of the olfactory epithelium may also be used for autologous or homologous transplants to treat other neurodegenerative diseases, disorders or abnormal physical states.

Precursor cells were also isolated from tongue and these may also be used for autologous or homologous transplants to treat neurotrauma or neurodegenerative diseases, disorders or abnormal physical states.

The stem cells or progenitor cells can be taken from an individual suffering from a neurodegenerative disease and then differentiated into neurons, astrocytes, oligodedrocytes for implantation into the nervous system of the individual. In a preferred mode of the invention, cells may be transplanted into the CNS, PNS, spinal cord or other damaged tissues.

Thus, this invention overcomes the needs outlined above in that the precursor cells of this invention (1) are accepted by the patient because they can be taken from the patient's own olfactory epithelium or tongue, (2) are safe in that the patient is not receiving cells or tissue from another source, (3) are effective in that the cells are of neural tissue origin and can be differentiated into neurons, astrocytes and oligodendrocytes for implantation and the cells survive during and after implantation, (4) offer the potential to provide long term relief of the symptoms associated with neurodegenerative diseases, and (5) would not raise objections to the ethics of their use.

Therefore, this invention relates to isolated and purified precursor cells of peripheral tissues with sensory receptors, such as the olfactory epithelium of a mammal (juvenile or adult). Under appropriate conditions, the precursor cells can differentiate into neurons, astrocytes or oligodendrocytes. The precursor cells may be transfected with a heterologous gene encoding, for example, a trophic factor. The precursor cells may then be implanted into the CNS, PNS, spinal cord or other damaged tissues of a patient and the heterologous gene expressed.

This invention also relates to neurons, astrocytes and oligodendrocytes differentiated from the precursor cells of this invention.

The invention also includes a pharmaceutical composition for use in implant therapy. The composition includes the precursor cells of this invention or neurons, astrocytes or oligodendrocytes differentiated from the precursor cells of this invention, in a pharmaceutically acceptable carrier, auxiliary or excipient. The composition may include one or more types of cells selected from a group consisting of precursor cells, neurons, oligodendrocytes and astrocytes.

A method of treating an individual suffering from a neurodegenerative disease is included within this invention. The method includes implanting the precursor cells of this invention, or the neurons, astrocytes or oligodendrocytes derived from the precursor cells of this invention, into the CNS, PNS, spinal cord or other damaged tissues of the individual. Another method consists of treating an individual suffering from a neurodegenerative disease by administering the pharmaceutical composition of this invention to the individual.

This invention also includes a method for isolating and purifying precursor cells from the olfactory epithelium of a mammal. The method includes (1) taking a sample of the olfactory epithelium from the mammal, (2) dissociating the sample into single cells, (3) placing the cells in culture, (4) isolating the cells which survive in culture. These isolated cells may be differentiated into neurons, astrocytes or oligodendrocytes. The precursor cells which survive in culture are spherical aggregates. The step of placing the cells in culture includes placing the cells in a tissue culture incubator in an appropriate medium. We isolate precursor cells from the tongue and other peripheral tissues with sensory receptors using a similar technique.

In this method, the mammal may be a human who is suffering from a neurodegenerative disease, disorder (such as neurotrauma) or abnormal physical state. The method may further include implanting the precursor cells or the neurons, astrocytes or oligodendrocytes differentiated from the neural stem cells, into the CNS, PNS, spinal cord or other damaged tissues of the human. In another case, the mammal is a human and is not suffering from a neurodegenerative disease or neurotrauma. Then, the method includes implanting the precursor cells or the neurons, astrocytes or oligodendrocytes differentiated from the precursor cells, into a second human who is suffering from the neurodegenerative disease or neurotrauma. The neurodegenerative disease may be one selected from a group consisting of Parkinson's disease, Alzheimer's disease, Huntington's disease and Multiple Sclerosis, while types of neurotrauma include stroke and spinal cord injury.

This invention also includes a kit for the treatment of a disease, disorder or abnormal physical state. The kit includes one or more types of cells including the precursor cells of this invention, or the neurons differentiated from these precursor cells, the astrocytes differentiated from these precursor cells and the neurons, astrocytes and oligodendrocytes differentiated from these precursor cells.

The invention also provides precursor cell cultures which may be used in toxicity testing, drug development testing or studies of genes and proteins. Precursor cell cultures may also be induced to produce healthy differentiated cells which may be used for toxicity testing or drug development testing. Toxicity testing is done by culturing precursor cells or cells differentiated from precursor cells in a suitable medium and introducing a substance, such as a pharmaceutical or chemical, to the culture. The precursor cells or differentiated cells are examined to determine if the substance has had an adverse effect on the culture. Drug development testing may be done by developing derivative cell lines, for example a pathogenic cell line, which may be used to test the efficacy of new drugs. Affinity assays for new drugs may also be developed from the precursor cells, differentiated cells or cell lines derived from the precursor cells or differentiated cells. The methods of performing toxicity testing and drug development testing are well known to those skilled in the art.

Precursor cells also provide a culture system from which genes, proteins and other metabolites involved in cell development can be isolated and identified. The composition of stem cells may be compared with that of progenitor cells and differentiated cells in order to determine the mechanisms and compounds which stimulate production of stem cells, progenitor cells or differentiated cells. Methods of isolating proteins and genes from cells are well known to those skilled in the art.

Other objects, features and advantages of the present invention will become apparent from the following detailed description. It should be understood, however, that the detailed description and the specific examples while indicating preferred embodiments of the invention are given by way of example only, since various changes and modifications within the spirit and scope of the invention will become apparent to those skilled in the art from this detailed description.

BRIEF DESCRIPTION OF THE FIGURES

The invention will now be described in relation to the figures.

DETAILED DESCRIPTION OF THE INVENTION

Figure 1A:
FIG. 1.
a) Bright field photograph of a small group of cells; 4 days in vitro ("DIV"). Scale bar=40 μm.
b) Bright field photograph of 3 floating olfballs; 12 DIV. Scale bar=200 μm.
c) Bright field photograph of 3 olfballs in the process of fusing; 12 DIV. Scale bar=200 μm.
d) Nestin staining of an olfball. 6 DIV and one day after plating down. Scale bar=30 μm.

The inventors have isolated multipotential precursor cells from the olfactory epithelium of mammals juvenile and adult mice, adult rat and humans). The isolated cells proliferate in culture, so that large numbers of precursor cells can be generated. In culture, these cells form floating spheres which are named "olfballs". These cells can be induced to differentiate into neurons, astrocytes, and oligodendrocytes by altering the culture conditions. The precursor cells can generate differentiated cells for use in autologous transplants for the treatment of certain neurodegenerative disorders or neurotrauma. For example, precursor cells may be differentiated into dopaminergic neurons and implanted in the substantia nigra or striatum of Parkinson's disease patients. They can also be used to generate oligodendrocytes for use in autologous transplants for multiple sclerosis. The precursor cells are easily accessible by biopsy from the olfactory epithelium, so they are a ready source of cells for autologous transplants. Finally, they could be used as autologous cellular vectors to introduce growth factors into the diseased or traumatized CNS, PNS, spinal cord and other damaged tissues.

The olfballs display some similarities to forebrain stem cells, but also possess some distinctive differences. In particular, (i) when olfballs differentiate in the presence of serum, almost half of the differentiated cells express neuronal markers, whereas differentiated forebrain stem cell neurospheres generate only a small percentage of neurons, (ii) significant numbers of dopaminergic neurons are found in all differentiated cultures of olfballs, whereas they are never found in cultures of forebrain stem cell neurospheres differentiated in serum, and (iii) many of the undifferentiated progenitor cells that are found in olfball cultures express glutamic acid-decarboxylase (GAD), a neurotransmitter enzyme that is expressed transiently in many neuroepithelial cells in vivo; in contrast, the only GAD-positive cells that derive from forebrain stem cell neurosphere cultures are neurons.

The precursor cells of this invention may be used to prepare pharmaceutical compositions which can be administered to humans or animals. Dosages to be administered depend on patient needs, on the desired effect and on the chosen route of administration.

The invention also relates to the use of the cells of this invention to introduce growth factors into the diseased, damaged or physically abnormal CNS, PNS, spinal cord or other damaged tissues. The precursor cells act as a vector to transport a recombinant molecule, for example, or to transport a sense or antisense sequence of a nucleic acid molecule. In the case of a recombinant molecule, the molecule would contain suitable transcriptional or translational regulatory elements.

Suitable regulatory elements may be derived from a variety of sources, and they may be readily selected by one with ordinary skill in the art. If one were to upregulate the expression of the gene, one would insert the sense sequence and the appropriate promoter into the vehicle. If one were to downregulate the expression of the gene, one would insert the antisense sequence and the appropriate promoter into the vehicle. These techniques are known to those skilled in the art.

Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. The recombinant molecule may be introduced into the precursor cells or the cells differentiated from the precursor cells using in vitro delivery vehicles such as retroviral vectors, adenoviral vectors, DNA virus vectors and liposomes. They may also be introduced into such cells in vivo using physical techniques such as microinjection and electroporation or chemical methods such as coprecipitation and incorporation of DNA into liposomes. The genetically altered cells may be encapsulated in microspheres and implanted in the CNS, PNS, spinal cord and other damaged tissues.

The following examples describe (i) the derivation of olfballs from postnatal mouse and adult mouse tissue, (ii) the derivation of olfballs from rat and human tissue, (iii) the use of olfballs to generate endogenous CNS cell types in the transplanted adult mouse brain, (iv) methods for genetically manipulating olfballs for use as therapeutic vectors, (vi) isolation of precursor cells from other peripheral tissues with sensory receptors such as tongue We characterize and use these cells using procedures similar to those used with olfballs. These studies provide us with novel tools for the treatment of the traumatized or diseased adult nervous system.

EXAMPLE 1

Figure 1B:
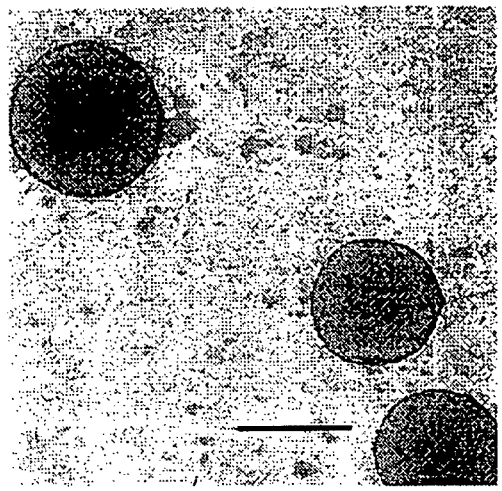
Figure 1C:
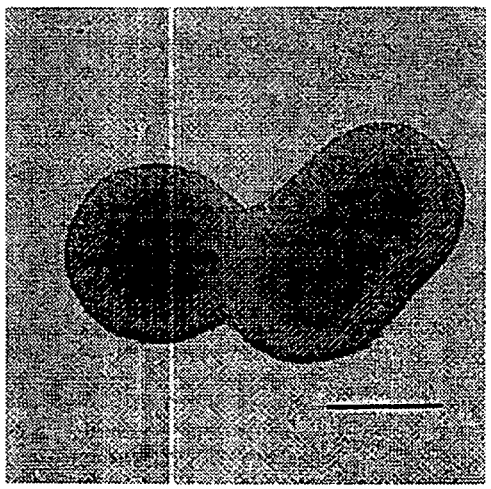

Isolating Multipotential Precursor Cells from Postnatal Olfactory Epithelium of Mice Postnatal mice were stunned with a blow to the head and then decapitated. The heads were sagitally sectioned with a razor blade. The olfactory epithelium of about 6 postnatal (P 1–9) mouse pups were stripped from the conchae, nasal septum, and vomeronasal organs using watch-maker forceps. This tissue was placed into 3 mls of media (DMEM/F-12 1:3 (Hyclone media) supplemented with 2% B-27 (Gibco), 20 ng/ml EGF (Collaborative Research), 0.1% fungizone, 0.5 ml/100 ml penicillin/streptomycin (Gibco). After epithelium from the postnatal pups was collected, the epithelium was teezed apart with watch maker forceps, releasing a large number of single cells. The media was transferred to a 15 ml tube, and 7 ml more media was added. The cells were dissociated into single cells, by titration with 10 ml plastic pipette (Falcon), and passed through a 60 micron filter (Gibco). Typically dissociated cells from the olfactory epithelium from 6 pups was plated into 2 50 ml tissue culture flasks (Falcon). The dissociated cells were then placed in 50 ml flasks in a 37° C., 5% CO2 tissue culture incubator. Two days later most cells in the cultures were dead or dying. However, a small number of large phase bright cells were present, most of which attach to the flask bottom. Over the next 2–6 days these cells divided and produced spherical aggregates which became larger over time. On day 4 (FIG. 1A) there were approximately 500 clusters of dividing cells per pup used in the original isolation (n=2 independent isolations). Most of these cellular aggregations lifted from the flask surface over the next few days (FIG. 1B). These floating spheres (olfballs) continued to grow and fused together to become macroscopic (FIG. 1C), reaching 100 microns in diameter if left for 10 days days in vitro. After 14 days in vitro, the diameter of the spheres was approximately 1 mm.

If EGF was not added to the media, small clusters of dividing cells were still seen by day 4, and some of these cells developed into olfballs, suggesting that the cells were producing trophic factors themselves in quantities which in some cases was sufficient for their proliferation.

Figure 1D:
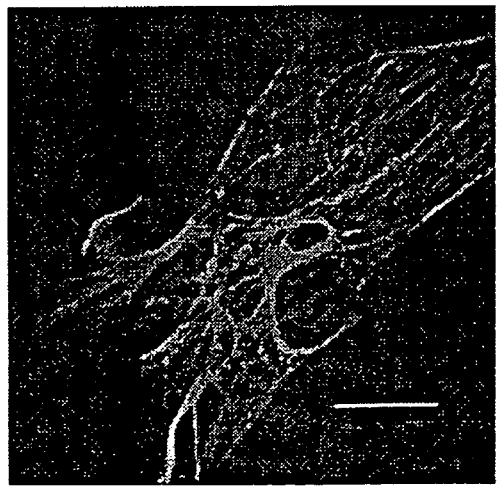

The cells in these dividing clusters expressed a marker for neural progenitor cells and neural stem cells, the intermediate filament protein nestin; at six days, olfballs were transferred to polylysine coated 35 mm dishes overnight in media containing 2% fetal bovine serum to facilitate the cells adhering to the substratum, and were processed for indirect nestin immunohistochemisty. Filamentous antibody staining was observed in almost all the cells in the clusters (FIG. 1D).

These nestin positive cells could also be passaged. Six days after isolation, the media (5 ml) was removed from the flasks. This media contained many olfballs that had lifted from the flask surface. The media containing olfballs was titturated with a fire polished pipette, thereby dissociating many of the cell clusters into single cells, and placed in a larger flask with an additional 15 ml of fresh media (total volume now 20 ml). After a further 6 days one quarter of the media was removed, the olfballs were again triturated, and put into a new flasks with 15 ml fresh media and EGF. These cells have been successfully passaged four times.

EXAMPLE 2

Figure 2A:
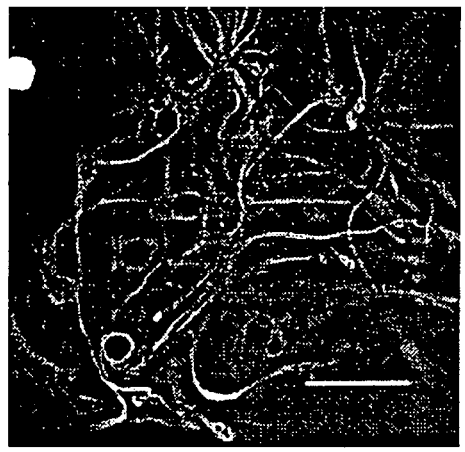
FIG. 2.
a) GFAP staining of differentiated olfballs. 16 days after plating down. Scale bar=50 μm.
b) GFAP staining of differentiated cells derived from olfballs which had been passaged twice. 16 days after plating down. Scale bar=50 μm.
c) GC staining of differentiated olfballs. 16 days after plating down. Scale bar=50/u.
d) Bright field of same field as shown in c). Scale bar=50 μm.
e) GC staining of differentiated olfballs derived from olfballs which had been passaged twice. 16 days after plating down. Scale bar=200 μm.
Figure 2B:
Figure 2C:
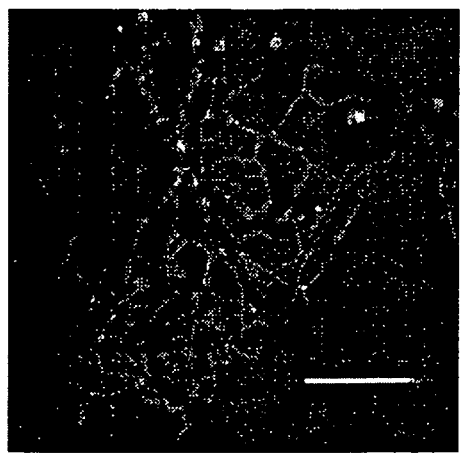
Figure 2D:
Figure 2E:
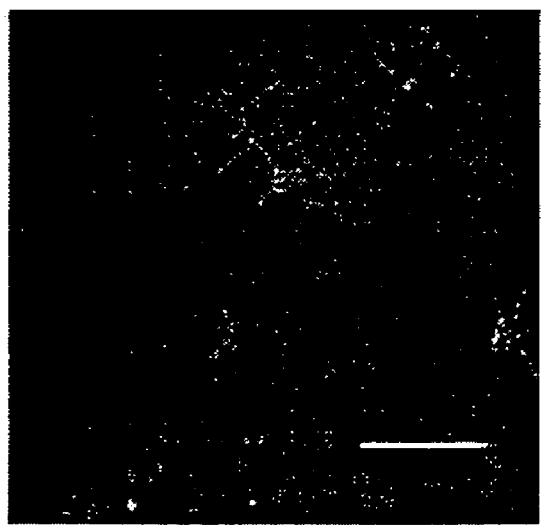
Figure 3A:
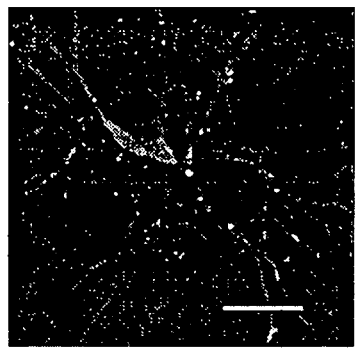
FIG. 3.
a) NF-160 staining of differentiated olfballs. 16 days after plating down. Scale bar=50 μm.
b) Bright field of same field as shown in c). Scale bar=50 μm.
c) LacZ staining of differentiated olfballs derived from T$\alpha$1:nlacZ mice (Gloster et al., 1994) that express a neuron-specific E. coli β-galactosidase marker gene. 16 days after plating down. Scale bar=50 μm.
d) TH staining of differentiated olfballs. 16 days after plating down. Scale bar=50 μm.
e) TH staining of differentiated olfballs derived from olfballs which had been passaged twice. 16 days after plating down. Scale bar=50 μm.
f) Bright field of same field as shown in e). Scale bar 50 μm.
g) βIII tubulin staining of differentiated olfballs. 16 days after plating down. Scale bar=100 μm.
h) NeuN staining of differentiated olfballs. 16 days after plating down. Scale bar=50 μm.
Figure 3B:
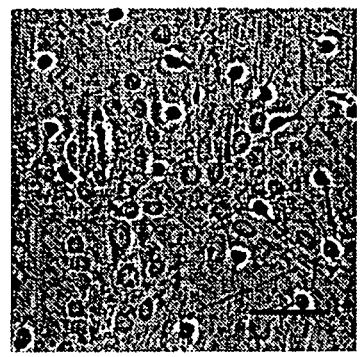
Figure 3C:
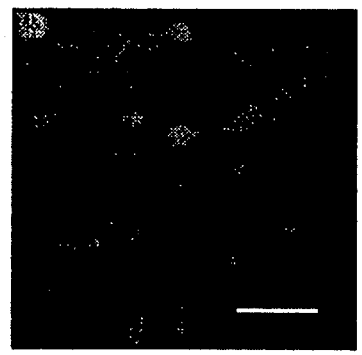
Figure 3D:
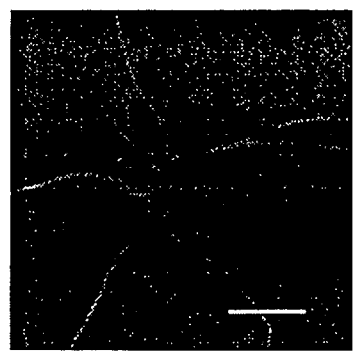
Figure 3E:
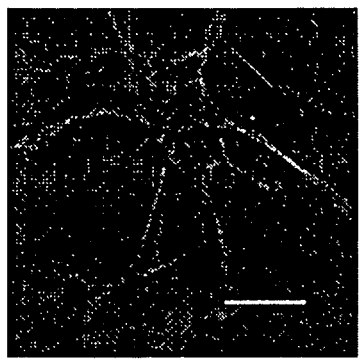
Figure 3F:
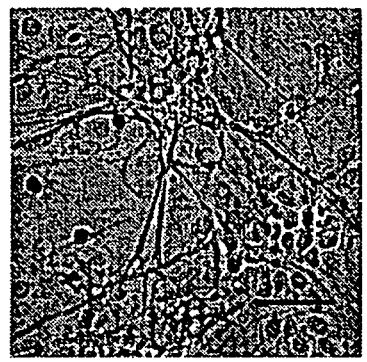
Figure 3G:
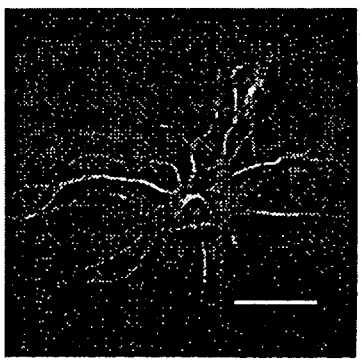
Figure 3H:

Differentiating Precursor Cells Into Neurons Astrocytes and Oligodendrocytes After the cellular clusters of Example 1 had been generated they could be differentiated into neurons, astrocytes, and oligodendrocytes. Clusters from cultures 7 to 14 days after isolation were plated down onto polylysine coated 35 mm culture dishes (Falcon) and 4 multiwell culture dishes (NUNC), in DMEM/F12 media containing 2% fetal bovine serum (Hyclone) and 2% B-27 (no EGF). Media was changed every 3–4 days. Over the next 6–19 days cells migrated out of the olfballs onto the dish surface. Some of these cells had the morphology of neurons, astrocytes, or oligodendrocytes. We determined the phenotype of these cells using marker antibodies to glial fibrillary acid protein (GFAP) (FIGS. 2A, B) for astrocytes, antibodies to neurofilament 160 (NF-160) (FIG. 3A), $\beta$ III tubulin (FIG. 3G), NeuN (FIG. 3H) for neurons, and antibodies to galactocerebroside (GC) (FIGS. 2C–E) for oligodendrocytes. Antibodies to tyrosine hydroxylase (TH) were used to identify dopaminergic, noradrenergic, and adrenergic neurons (FIGS. 3D–F). Dopamine $\beta$-dehydrogenase (DBH) was also used for noradrenergic and adrenergic neurons.

Immunohistochemical procedures. With the exception of GC immunohistochemistry, culture dishes were washed twice with TBS (Tris Buffered Saline; 10 mM Tris, 150 mM NaCl, pH 8), then fixed with 4% paraformaldehyde, rinsed in three times with TBS, blocked with TBS plus 2% goat serum (Jackson ImmunoResearch), and 0.1% Triton-X (Sigma) for 30 min, then incubated with primary antibody in TBS plus 2% goat serum, rinsed 3 times with TBS, incubated in secondary antibody in TBS plus 2% goat serum, rinsed 3 times and then viewed under a Zeiss Axiovert 100 florescence inverted microscope. The antibodies to GFAP (Boehringer Mannheim), $\beta$III tubulin (Sigma and a gift from Dr. D. Brown, U. Ottawa), NeuN (Dr. R. Mullen), NF-160 (American Tissue Culture Collection) were monoclonals used at concentrations of 1:200; 1:25; 1:10, and 1:1 respectively. Antibodies to nestin (a gift from Dr. Ron MacKay (Nation Institute of Health), TH (Eugenetech), and DBH (Eugenetech) were rabbit polyclonals used at concentrations of 1:1000, 1:200, and 1:200 respectively. Secondary antibodies were Cy3 conjugated goat anti-mouse (Jackson ImmunoResearch) and Cy3 conjugated goat anti-rabbit (Jackson ImmunoResearch), and were used at 1:1500. For double-labelling experiments FITC goat anti-mouse (Jackson ImmunoResearch). GC immunohistochemistry, living cultures were incubated with a DMEM media; HEPES; 5% HS (heat inactivated horse serum), and 1:10 GC antibody (BRD1; a gift of Dr. B. Juurlink U. Sask.) for 30 min at 37° C., rinsed 3 times with the media/HEPES/HS, fixed with 4% paraformaldehyde for 15 min, rinsed 3 times in TBS, incubated in Cy3 conjugated goat anti-mouse antibody (1:1500) for 2 hr., finally rinsed 3 times in TBS. Cultures processed for immunohistochemistry without primary antibodies revealed no staining.

Astrocytes, neurons, and oligodendrocytes were found. We also cultured olfballs from transgenic mice which express $\beta$-galactosidase off of the neuron specific promoter T$\alpha$1 $\alpha$-tubulin, which allowed us to use staining with the ligand X-gal antibodies for $\beta$-galactosidase as an additional neuronal marker (FIG. 3B, 3C).

Since the differentiated cells abutted each other and were piled up on top of each other in the center where the olfball originally attached, it was not possible to count the number of cells expressing each marker. The majority of cells that migrated out of the clusters were GFAP positive while a large number of cells were either NeuN or lacZ positive. A lower number of cells were NF-160 positive, $\beta$ III tubulin, TH, GAD or GC positive. Therefore the olfballs could differentiate into neurons, astrocytes and oligodendrocytes. While a few of the $\beta$III tubulin positive cells had complex morphologies (FIG. 3A), most were simpler, possessing only a few neurites. The TH positive cells were the most morphologically complex cells in the cultures, with numerous neurites extending from the cell body (FIGS. 3D, E). These TH positive cells are probably dopaminergic neurons and not noradrenergic or adrenergic neurons, since no cells were found to be DBH positive. Significantly, no TH, GFAP or GC positive cells have ever been reported in vivo in the nasal epithelium. Therefore the olfactory derived nestin positive olfball cells could be differentiated into cell types never found in the olfactory epithelium-oligodendrocytes, astrocytes, GABAergic neurons, and dopaminergic neurons. The coexpression of astrocytic and neuronal markers has been reported for differentiated cells derived from EGF-generated brain-derived progenitor cells (Peel et al., 1995). While most cells were either lacZ or GFAP positive, there were a few cells which were both lacZ and GFAP positive, however none of the TH positive cells were also GFAP positive. Therefore while cells may transiently express both neuronal and glial markers during their differentiation program, fully differentiated morphologically complex neurons express only neuronal markers.

Like the original olfballs, the passaged olfballs could also be differentiated into neurons, astrocytes, and oligodendrocytes. Olfballs which had been passaged twice were plated down on polylysine coated dishes. The olfballs cells migrated out and spread out over the dish's surface, and after 16 days were immuno-positive for GC (FIG. 2E), GFAP, $\beta$III tubulin, NeuN, lacZ, and TH. The proportion of cells positive for the various markers was similar to that seen in the differentiated cultures from the original cultures.

EXAMPLE 3

Isolating Multipotential Precursor Cells from Olfactory Epithelium of Adult Mice and Adult Rats Similar proliferating cells were also isolated from adult mouse and rat olfactory epithelium and vomeronasal organs. We developed techniques for reproducibly culturing, passaging, and differentiating the adult olfballs, on the basis of our experience with their juvenile equivalents. As part of this aim, we (i) characterized the growth factor and media requirements for the adult cells to proliferate in culture, and (ii) characterized the growth factor and substrate requirements for the differentiation of oligodendrocytes and dopaminergic neurons from both adult and juvenile olfballs. We were informed in these studies by similar work on EGF- and FGF-dependent stems cells from the CNS, since olfballs likely respond to at least some of the same growth factors. The adult isolation procedures were essentially the same as for the postnatal olfballs (described in examples 1 and 2).

Figure 4A:
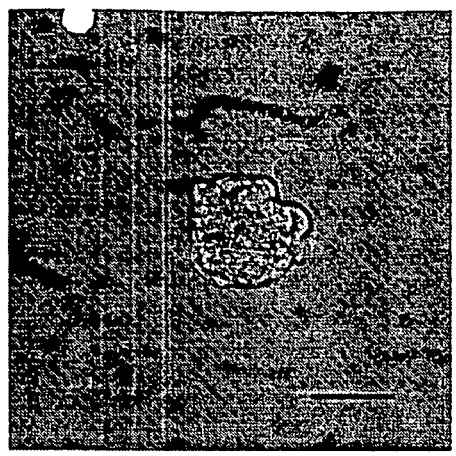
FIG. 4
a) Bright field photograph of a small floating adult derived olfball; 8 DIV. Scale bar=50 μm
b) Bright field photograph of a larger adult derived floating olfball; 15 DIV. Scale bar=50 μm
c) nestin staining of a differentiated cell derived from an adult olfballs; 16 days after plating down. Scale bar=25 μm
FIG. 5
Limiting dilution curve. Cells were plated at 700 to 7000 cells per well, cultured for 14 days in vitro, and then examined for the presence of olfballs. The fraction of wells without olfballs was plotted against the number of cells plated. Based upon the Poisson distribution, the probability of a well not having an olfball at the 0.37 level (1/e) indicates that 1 of every 9000 cells plated has the capacity to generate an olfball. The correlation value of the line is r=−0.992.
Figure 4B:
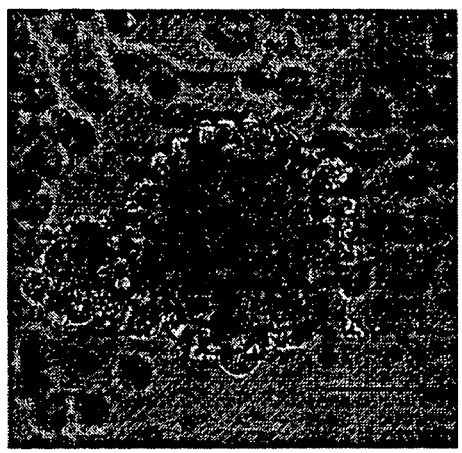

Adult mice and rats were anaesthetized with injected with an overdose of somnitol, and then decapitated. The olfactory and vomoeronasal organ epithelia were stripped from the conchae and nasal septum and incubated in F12/DMEM culture media for 1 or 2 days after their dissection and prior to the rest of the isolation procedure (B). After this incubation, the epithelia was dissociated in an identical manner as the postnatal epithelia. Two days after the isolation almost all the cells were dead with the exception of a very few large phase bright cells. These cells divided over the next few days, forming small clusters of dividing cells similar to those seen in the postnatal cultures (FIGS. 4A, B). These also grew to give rise to the large floating clusters which were routinely seen in the postnatal cultures. After 6 divisions some of these clusters began to differentiate and spread out over the flask's surface, while some other clusters which had floated reattached to the surface and then differentiated. (These cells multiplied to produce the small balls or cells, but did not grow to form the large balls of cells like the postnatal cultures). We passaged these cells using the same procedure as that described above with respect to the cells isolated from postnatal olfactory epithelium.

Figure 4C:
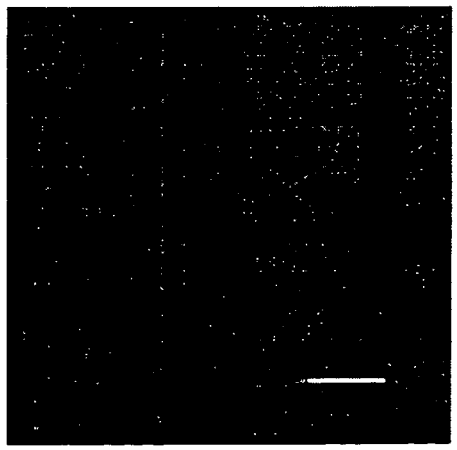

These proliferating cells from the adult were also nestin positive. 10 days after their initial isolation the cells were transferred to polylysine coated dishes with 2% fetal bovine serum (FBS). Two hours later the cells were processed for nestin immunohistochemistry (FIG. 4C).

After the cellular clusters of this Example had been generated they could be differentiated into neurons and oligodendrocytes. Clusters from cultures 7 day after isolation were plated down onto polylysine coated 35 mm culture dishes and 4 multiwell culture dishes, in media containing 2% fetal bovine serum and 2% B-27 (no EGF). Over the next month cells migrated out of the olfballs onto the dish surface. We determined the phenotype of these cells using marker antibodies to glial fibrillary acid protein (GFAP) for astrocytes, antibodies to βIII tubulin for neurons, antibodies to TH for dopaminergic neurons and antibodies to galactocerebroside (GC) for oligodendrocytes.

Neurons, and oligodendrocytes were found, although the number of these cells was much lower than the number obtained from the neonate. The phenotype of these adult derived differentiated cells was assessed using indirect immunohistochemistry. The cells isolated from the adult were differentiated into βIII tubulin positive cells (neurons), tyrosine hydroxylase positive cells (dopaminergic neurons), galactocerobroside positive cells (oligodendrocytes). No astrocytes (GFAP positive) cells were found. Therefore the adult derived olfballs could differentiate into neurons and oligodendrocytes.

EXAMPLE 4

Precursor Cells Differentiate Into Neurons When Transplanted Into Adult Brain The major potential therapeutic use for olfballs is autologous transplantation into the injured or degenerating CNS, PNS, spinal cord and other damaged tissues, either to replace lost cell types and/or as vectors for expression of therapeutic molecules. Transplantation experiments determine the fate of transplanted olfactory-derived precursor cells. The precursor cells can differentiate into neurons when transplanted into the adult brain. To this end, we transplant mouse derived precursor cells into brains of immunosuppressed adult rats and identify which of the transplanted cells differentiate into neurons, using double labelling with the mouse specific and neuron specific antibodies (such as those which recognize neuron specific enolase and neuron specific βIII β-tubulin). A similar approach has proved successful in the study of transplanted brain-derived stem cells (Winkler, Hammang, and Bjorklund, 1996).

In order for these stem cells to be useful for transplantation to treat neurodegenerative diseases it is necessary to induce the differentiation of the appropriate neuronal phenotype, such as dopaminergic neurons in the case of Parkinson's disease. Therefore, initially we determine if the precursor stem cells transplanted into lesioned and unlesioned striatum and substantia nigra, differentiate into dopaminergic neurons in response to signals from their new environment, as they do when they differentiate in vitro. Brain sections are double labelled with a mouse specific antibody and antibodies to tyrosine hydroxylase to reveal dopaminergic neurons derived from the transplanted cells. Transplants into neonatal rat brains show that a more immature host environment is able to induce dopaminergic differentiation.

We transplanted olfballs into the denervated and intact striatum of adult rats. Specifically, we unilaterally destroyed the dopaminergic innervation of the adult striatum by a local infusion of 6-hydroxydopamine, under conditions where noradrenergic neurons are spared. Several weeks following this lesion paradigm, olfballs were transplanted into both the intact and lesioned striatum, and one week later, the fate of the transplanted olfballs was determined immunocytochemically. These studies demonstrated that transplanted olfballs can differentiate into tyrosine-hydroxylase-positive neurons in vivo, as they can in vitro. Given that the primary deficit in Parkinson's disease is a loss of dopaminergic innervation of the striatum due to neuronal loss, these preliminary studies raise the exciting possibility that olfballs provide an autologous source of dopaminergic neurons with which to treat this disease.

We characterize the neuronal and glial cell types that are generated by olfballs transplanted into the adult striatum. In order to definitively identify the progeny of the transplanted olfballs, we (i) derive olfballs from transgenic mice expressing β-galactosidase from either the Tα1 α-tubulin and/or myelin basic protein promoters, thereby marking both transplanted neurons and oligodendrocytes, and (ii) rely upon the use of a mouse-specific antibody to distinguish all of the transplanted cells. Alternatively, we tag the olfballs with β-galactosidase marker gene in vitro prior to their transplantation. We then double-label cells immunocytochemically with markers for the different cell types, such as tyrosine hydroxylase for dopaminergic neurons, galactocerebroside for oligodendrocytes, and GFAP for astrocytes. Using this approach, we tagged the stem cells with BrdU, followed them and found double labelled GFAP and TH-positive cells.

EXAMPLE 5

Precursor Cells Differentiate In Vitro

We determine whether there are in vitro conditions which promote the differentiation of precursor cells into different neural phenotypes. To identify such conditions the effect of a variety of substrates, conditioned media, and growth factors are tested. We test the substrates laminin, fibronectin, heparin proteoglycans. Conditioned media we test includes media from cultures growing neonatal heart cells, astrocytes and stiatal neurons. We test the growth factors NGF, BDNF, NT-3, NT-4/5, bFGF, EGF, TGFα, TGFβ, LIF (leukemia inhibitory factor) and CNTF (ciliary neurotrophic factor), PDGF, GDNF and neurturin.

EXAMPLE 6

The Extent To Which the Local Environment Determines Neural Cell Fate

It is useful not only to generate neurons, but also oligodendrocyytes for transplantation therapy. Another basic question that we address is the extent to which the local environment determine neural cell fates. Outside of their normal environment, olfactory-derived progenitor cells are not restricted to differentiating into olfactory neurons. This experiment determines whether the converse is also true. We determine whether brain-derived stem cells co-cultured with olfactory epithelium differentiate into olfactory neurons. Co-cultures experiments with various explants and stem cells derived from various nervous system sources provide.

EXAMPLE 7

Human Precursor Cells Derived From Human Nasal Epithelium Much Information on the Role of the Local Environment in Determining Cell Fate If olfactory-derived neural stem cells are to be used for autologous transplants for the treatment of neurodegenerative disorders it is necessary to show that they can be generated from human nasal epithelium. During certain neurosurgical operations nasal tissue is removed. We isolate human olfactory-derived neural stem cells from this tissue as it becomes available. We use the same procedures as we used to isolate the neural stem cells from the neonate and adult mice. As is known to those skilled in the art, work on primate and human neurospheres with regards to culture conditions provide information on optimizing proliferation of cell spheres and specific cell types.

EXAMPLE 8

Transfection Of Olfactory-Derived Precursor Cells And Using Precursor Cells In Autologous Cellular Vectors To Introduce Growth Factors Into The Diseased Or Traumatized CNS, PNS, Spinal Cord And Other Damaged Tissues As a therapy for neurodegenerative diseases, transplanted cells may have to be genetically engineered so that they can survive the insults that caused the original neurons to die, and therefore it would be advantageous to be able to transfect precursor cells. In addition, the transfected olfactory progenitor could be used as vectors for introducing biologically active molecules into the brain of patients with neurodegenerative disorders. If olfballs are to be used as autologous transplantation vectors for expression of therapeutic molecules, it is essential to develop mechanisms for genetically manipulating them. We determine whether recombinant adenovirus vectors can be used for this purpose. We have previously used recombinant adenovirus to manipulate both postmitotic sympathetic neurons and cortical progenitor cells, with no cytotoxic effects when used under controlled conditions. We infect olfballs with a β-galactosidase-expressing adenovirus, and determine (i) how long the transduced marker gene is expressed, and (ii) whether this manipulation affects the growth and/or differentiation of olfballs in vitro. Then we transplant β-galactosidase-expressing olfballs in vivo, and measure the same parameters. Finally, we use recombinant adenovirus to overexpress brain derived neurotrophic factor ("BDNF") or GDNF in olfballs, and determine (i) whether autocrine BDNF or GDNF causes increased survival and differentiation of olfball-generated neurons in vitro or in vivo, (ii) whether autocrine BDNF causes increases numbers of dopaminergic neurons to differentiate from olfballs in vitro or in vivo, and (iii) whether BDNF-expressing or GDNF-expressing olfballs transplanted into the substantia nigra or striatum can protect endogenous dopaminergic neurons from chemical lesions. We pursue this experiment to effectively manipulate these stem/progenitor cells using recombinant adenovirus.

For example, if a trophic factor was useful in treating a neurodegenerative disorder, then neural progenitor cells or neural stem cells transfected with genes coding for the trophic factors, could be transplanted into a patient to provide a continuous source of the trophic factor at the transplantation sight. We use various strategies to transfect the stem cells including lipofectamine and viral transfections including herpes and adenovirus. We use lipofectamine and adenovirus mediated transfection strategies, which are well known to researchers in the field, to transfect the stem/progenitor cells. For lipofectamine transfections, we follow the standard protocol as outline in the lipofectamine product information sheet which comes with the lipofectAMINE Reagent purchased from Gibco. For adenovirus mediated transfections we follow the procedures outlined in Gage et al., 1995, Le Gal et al. 1993 and Slack and Miller, 1996.

EXAMPLE 9

Figure 5:
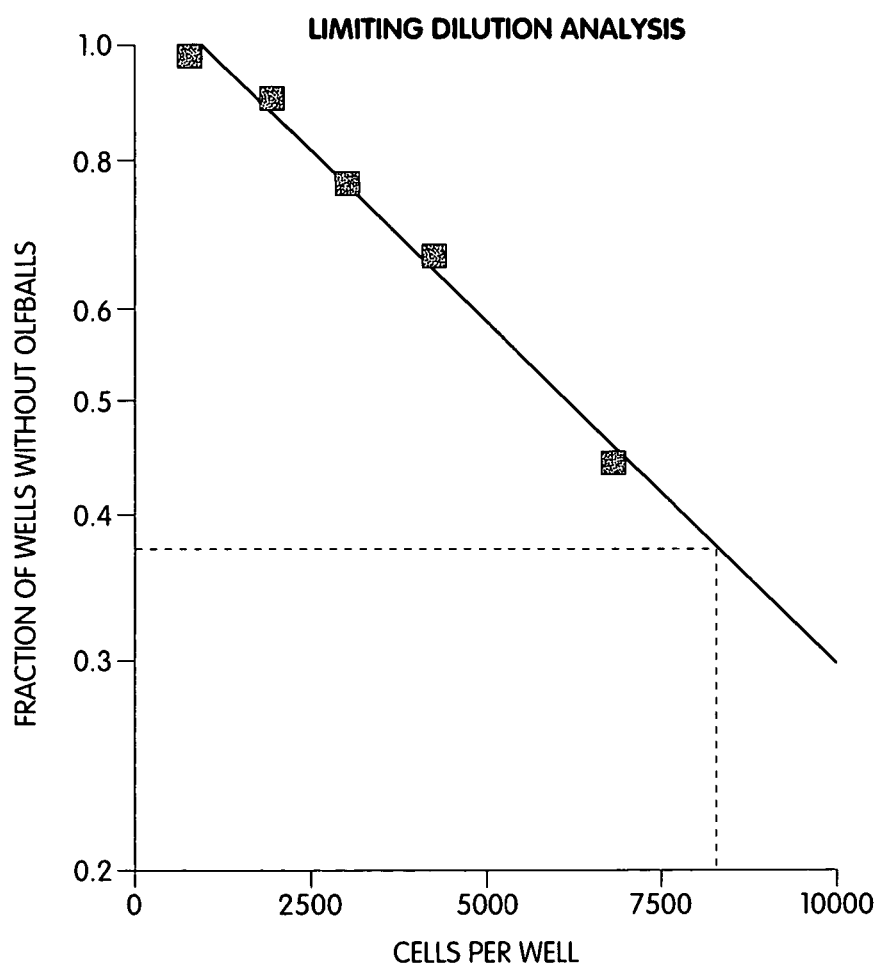

Limiting Dilution Analysis of Isolation And Transplantation Of Accessible Multipotential Neural Progenitor Cells From The Olfactory Epithelium To determine whether individual olfballs derived from single cells, we performed limiting dilution analysis. This analysis demonstrated that the limiting dilution curve was linear, displaying single hit kinetics, indicating that individual olfballs were clones of single cells. Moreover, this analysis demonstrated that cells capable of giving rise to olfballs were present at a frequency of approximately one in 9000. Differentiation of these individual olfballs demonstrated that they were multipotent, as were olfballs in mass cultures. Specifically, double-label immunocytochemistry revealed that olfballs derived from single cells were capable of generating astrocytes, oligodendocytes, and TH-positive neurons (FIG. 5). Cells positive for i) GFAP and GC, ii) GFAP and TH, and iii) GC and TH were generated. Thus, approximately one in every 9000 cells from the dissociated olfactory epithelia is capable of generating an individual multipotent olfball.

To determine whether individual olfballs derived from single cells, we performed limiting dilution analysis (Lefkowitz & Waldman, 1989). Specifically, diluted, dissociated cells from neonatal olfactory epithelia were cultured into 96 well plates, and the presence or absence of individual olfballs scored after 14 days (Bellows and Aubin, 1979). This analysis demonstrated that the limiting dilution curve was linear, displaying single hit kinetics, indicating that individual olfballs were clones of single cells.

For the limiting dilution experiments, olfactory epithelia from P5 mouse pups were dissociated and cultured as described above, except that the cells were plated in 96 well dishes at cell densities ranging from 700 to 7000 cells per well. After 14 days in culture the wells were examined for the presence or absence of olfballs. Differentiation of the solitary olfballs was performed as for the mass cultures described above, and the wells labelled immunohistochemically as described above, with primary antibodies to the following combinations of antigens; GFAP and TH, GC and TH, and GFAP and GC.

EXAMPLE 10

Genetic Modification of Olfactory Precursor Cells

As discussed above, a number of studies have demonstrated that adenovirus-based vectors can effectively transduce postmitotic neurons of the central nervous system (CNS) in vivo, and cells derived from the CNS in vitro (Le Gal et al., 1993, for review see Slack and Miller, 1996).

Figure 6:
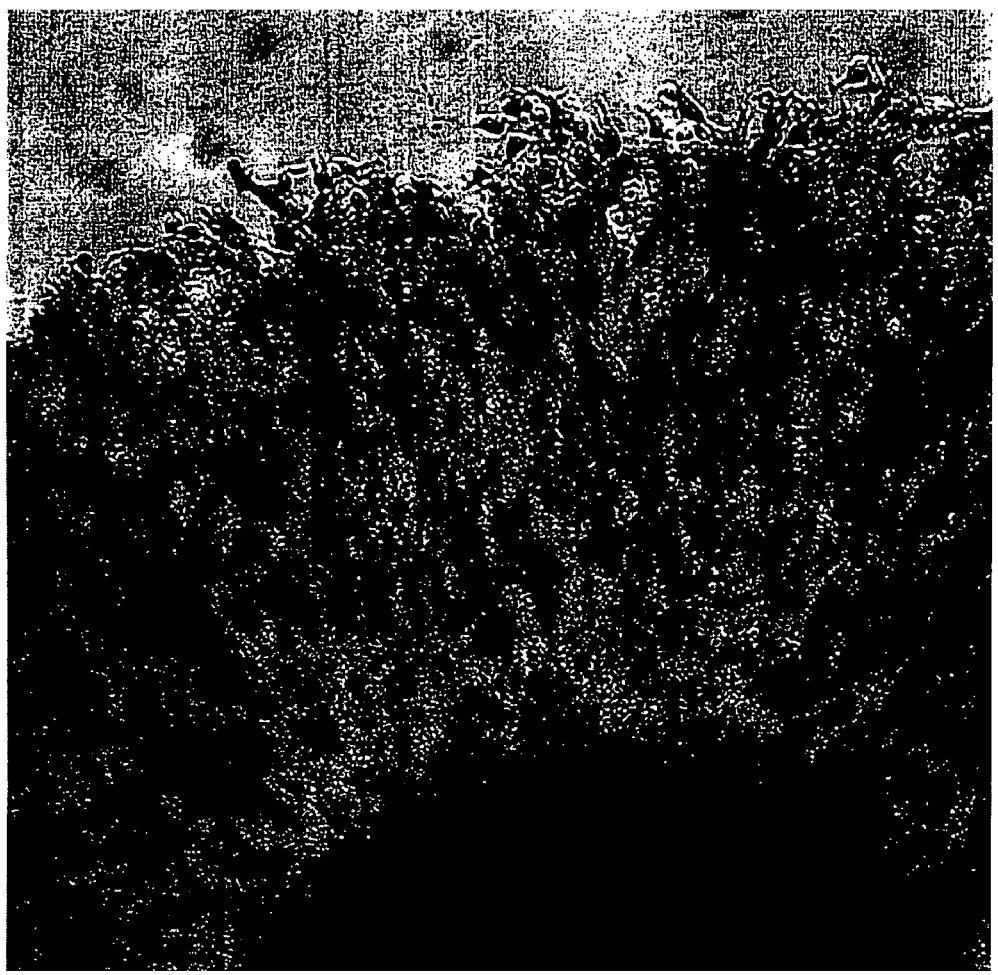
FIG. 6
Demonstration that the olfballs can be genetically modified. Olfballs were plated on polylysine in the presence of 2% FBS. CMV-β-galactosidase adenovirus was added at an MOI (Multiplicity of infection) of 25. Three days later the cultures were X-gal stained (standard histochemical technique to reveal cells expressing β-galactosidase), and 90% of cells were found to be expressing β-galactosidase.

In some circumstances it would be important to modify neural progenitor cells prior to their transplantation as therapy for neurodegenerative diseases, since the transplanted neurons may have to be genetically engineered to survive the insults that caused the original neurons to die. Olfactory precursor cells can be transfected using the adenovirus gene transfer system. We established that the olfactory epithelial-derived stem cells can be successfully transfected with high efficiency and low toxicity, using β-galactosidase as a marker gene (FIG. 6). A recombinant adenovirus carrying the β-galactosidase reporter gene inserted in the deleted E1 region was used in transfection experiments.

Multiplicity of infection (MOI) was calculated based on titration on cells for adenovirus-based vectors, and represents the number of plaque-forming units added per cell.

Staining for expression of the β-galactosidase marker gene was performed. Cells were fixed with 0.2% glutaraldehyde in PBS (pH7.4) for 15 min at 4° C. After two washes with PBS, cells were incubated for 18 h in X-gal stain (2 mM $MgCl_2$, 1 mg/ml X-gal, 5 mM $K_3Fe(CN)_6$, and 5 mM $K_4Fe(CN)_6$ in PBS (pH 7.4). To estimate the percentage of cells that were infected, the total cell number and lacZ-positive cells were counted in five random fields. The data were expressed as the average of two separate experiments with error bars representing the range.

EXAMPLE 11

Determination of the Intrinsic Factors Such as Transcription Factors that Regulate Cell Fate Determination To address whether candidate transcription factors, which have been identified in various experimental systems, can regulate neural fate decisions we transfect these factors into the olfactory epithelium-derived stem cells using the adenovirus gene transfer system.

We transfect the olfactory epithelium derived stem cells with the candidate transcription factors including IsI1, en-1, en-2 and nurr, which have been implicated in regulating motoneuron and striatal phenotypes. With an understanding on how intrinsic and extrinsic factors regulate neural cell fate decisions, it will be possible to induce the differentiation of the specific neural cell types required for neuronal transplant therapy.

EXAMPLE 12

Characterizing Olfactory Epithelial Derived Precursor Cells

We characterize the growth and differentiation of olfactory epithelia (OE) derived precursor cells, and their potential for use in transplantation therapy for neurodegenerative diseases. We previously isolated an EGF dependent population of multipotential neural precursor cells from the olfactory epithelium, and demonstrated that they can differentiate into CNS phenotypes including astrocytes, oligodendrocytes, and neurons. We characterize these precursor cells, the intrinsic and extrinsic factors which regulate the neural cell fate these cells adopt upon differentiation, and the potential for using these cells in transplantation therapy. We isolate stem cells from a patients olfactory epithelium, expand these in culture, differentiate them into the desired neural phenotype, and then transplant these cells back into the patient to help reverse the functional deficit. This strategy avoids problems associated with immunorejection since the transplanted cells are derived from the patients themselves.

We determine whether i) there is more than one population of olfactory epithelium precursor cells ii) these precursor cells are in fact stem cells iii) there are any negative changes associated with long term culture and iv) whether these cells can be isolated from human olfactory epithelium. We determine whether there is more than one population of precursor cells in these cultures analogous to the quiescent and relatively quiescent populations of brain derived stem cells, by limiting dilution analysis using trophic factors, which have been previously shown to support the proliferation of stem cells isolated from various regions of CNS such as EGF, TGF, and bFGF. We look for additive and synergistic interactions between the trophic factors. We demonstrated that these cells are multipotential and can be passaged up to 5 times, however, we propagate them over longer periods of time, while still retaining their multipotentiality. We also examine whether there are any cytogenetic changes or changes in growth characteristics after repeated passaging, to rule out possible neoplastic changes accompanying long term culture. We isolated olfactory epithelium derived stem/progenitor cells from mice and rats. We generate olfactory epithelium derived stem cells from humans olfactory epithelium, to demonstrate the feasibility of using autographs in the treatment of neurodegenerative disease.

EXAMPLE 13

Inducing Human Precursor Cells to Differentiate into Neurons

The experiments to induce human cells to differentiate into neurons, astrocytes, and oligodendrocytes are done in the same manner as the mice experiments (see example 2–3).

We induce precursor cells to differentiate into neurons by culturing them with growth factors. This is done similarly to the differentiation of precursor cells in example 2.

We demonstrated that OE derived stem/progenitor cells can differentiate in the same culture into oligodendrocytes, astrocytes, and neurons. We analyze the roles of trophic factors. Extracellular substrates are tested which we show are implicated in regulating differentiation of neural cell types in vitro and in vivo. Specifically, we demonstrate the effects of brain-derived neurotrophic factor (BDNF), ciliary neurotrophic factor (CNTF), triiodothyronine (T3), bone morphogenetic proteins (BMPs), platelet-derived growth factor (PDGF) and sonic hedgehog (SH). We identify growth factors that direct OE-derived stem cells to differentiate into specific cell types.

EXAMPLE 14

Inducing Human Precursor Cells to Differentiate into Astrocytes

We induce precursor cells to differentiate into astrocytes by culturing them with growth factors. This is done similarly to the differentiation of precursor cells in example 2.

EXAMPLE 15

Inducing Human Precursor Cells to Differentiate into Oligodendrocytes

We induce precursor cells to differentiate into oligodendrocytes by culturing them with growth factors. This is done similarly to the differentiation of precursor cells in example 2.

EXAMPLE 16

Using Neural Stem Cells or Neuronal Progenitor Cells in Autologous Transplants In Treatment of Parkinson's Disease We grow olfactory epithelial derived stem cells in vitro and differentiate these cells into specific neural cell types. These cells are useful therapeutically in the treatment of neurodegenerative diseases such as Parkinson's disease and multiple sclerosis. We implant dopamingeric neurons differentiated from precursor cells into the substantia nigra or the striatum of patients having Parkinson's Disease.

Figure 7A:
FIG. 7
Generation of TH-positive neurons upon transplantation of olfballs into the adult rat striatum. The striatum of adult rats was unilaterally denervated using 6-hydroxydopamine to eliminate dopaminergic fibers, and neonatal olfballs were transplanted into the striatum of the same animals. (a) With transplants of olfballs from T$\alpha$1:nlacZ mice, β-galactosidase positive nuclei (arrows) are detected along the graft tract. (b) A complex TH-positive neuron (arrow) with multiple processes (arrowheads). (c) A cluster of morphologically simple TH-positive cells that are double-labelled with BrdU. Note the black speckled appearance of the BrdU-labelling (arrow). (d) A TH-positive neuron (arrowhead) with a single process whose nucleus is double-labelled with BrdU (arrow). In this case, the BrdU staining fills the entire nucleus. Scale bar: a=100 μm, b,c=25 μm, d=5 μm.
Figure 7B:
Figure 7C:
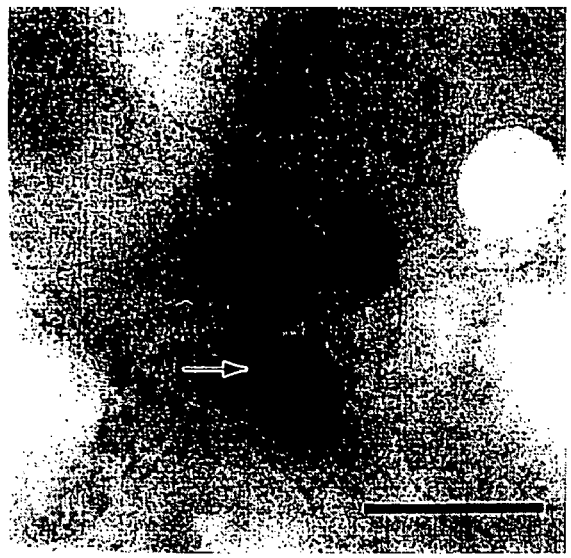
Figure 7D:

The adult olfactory epithelium could be used as an autologous source of stem/progenitor cells for cellular replacement therapy in the diseased or traumatized central nervous system. We focused on TH-positive neurons, which are lost in Parkinson's disease (17), and which could be differentiated from adult and neonatal olfballs, as shown here. To perform these experiments, the dopaminergic innervation to the adult rat striatum was first unilaterally lesioned with the chemotoxin 6-hydroxydopamine, and the efficacy of the lesions was tested two weeks later by amphetamine-induced rotational behavior (18). Two days prior to transplantation, rats were immunosuppressed with cyclosporin. Olfballs were then stereotactically injected into the caudate-putamen complex on both the lesioned and unlesioned sides (18). Sixteen days following transplantation, animals were sacrificed, and sections of the striatum were analyzed immunocytochemically for nestin and TH (19). Five of 8 animals received successful injections of olfballs in the striatum. Of these, 4 animals showed evidence of a nestin-positive tract on both the lesioned and unlesioned sides, although tracts on the lesioned side appeared to be more intensely nestin-immunoreactive (data not shown). On adjacent sections, TH-positive cells were observed confined to an area close to the transplant tract on both the lesioned and unlesioned side (FIGS. 7b–d). As many as 25–30 TH-positive cells were identified on each section. Cells varied in morphology from small round cells without processes, which may be neuroblasts or early postmitotic neurons, neurons with a single process, or a minority of neurons that were morphologically complex with multiple fine processes (FIG. 7b). In some cases, the processes of these TH-positive neurons extended into the striatum for distances of up to 300 $\mu$m. However, the cell body size of even the morphologically-complex TH-positive neurons were small relative to adult dopaminergic neurons of the substantia nigra.

To confirm that these TH-positive neurons derived from the olfballs, we performed two sets of experiments in which the transplanted cells were "tagged". In one set of experiments, transplanted olfballs were derived from Ta1:nlacZ transgenic mice (21), in which the neuron-specific Ta1 a-tubulin promoter drives expression of a nuclear-localized β-galactosidase marker gene. Immunocytochemical analysis of animals receiving the transgenic olfballs (18) revealed the presence of β-galactosidase-positive neurons within the transplant tract (FIG. 7a), confirming that the transplanted olfballs generated neurons in vivo as they did in vitro. In a second set of experiments, olfballs were labelled with BrdU for 18 hours, washed to remove the BrdU label, and the labeled cells transplanted unilaterally into the 6-hydroxy-dopamine-lesioned striatum of animals (10 rats/4 mice) prepared as described (18). Immunocytochemical analysis with anti-BrdU (22) revealed that all animals showed evidence of BrdU-positive transplant tracts. This BrdU-labelling took the form of a few blue-black nickel DAB labelled speckles (FIG. 7c), or a coalescent solid nuclear pattern identified within a brown cytoplasmic background (FIG. 7d).

Immunocytochemistry with anti-GFAP revealed that, in both xenografts and allografts, GFAP-positive cells with heterogeneous morphology were concentrated at the transplant site, but were also present in moderate amounts over the entire ipsilateral hemisphere, with additional scattered reactive astrocytes seen in the contralateral hemisphere. GFAP-BrdU double-labelled cells were present mainly within or close to the transplant tract, and varied in morphology from small, round cells with only a few processes, to large polygonal or fusiform cells with multiple processes. Immunocytochemistry with anti-TH revealed that TH-BrdU double-labelled cells were also present, although these were few in number relative to GFAP-BrdU positive cells. BrdU-TH double-labelled cells were mainly small to medium-sized without processes (FIG. 7c), although some examples of double-labeled cells with processes were found within (FIG. 7d) and adjacent to, the transplant tract. Thus, olfballs generated astrocytes and neurons in vivo, and a subpopulation of the latter were TH-positive. Together, these findings show that multipotent stem/progenitor cells derived from the olfactory epithelium are capable of generating cell types never found within the olfactory epithelium, including oligodendrocytes and TH-positive neurons. Moreover, TH-positive neurons can be generated not only in culture, but also in vivo in neural transplants. The implications of these findings are two-fold. Similar stem/progenitor cells can be derived from biopsies of the olfactory epithelium of adult Parkinson's disease patients, and used as an autologous source of neurons for transplantation. Current sources of dopaminergic neurons for neural transplantation are derived from human fetal tissue, a nonautologous source that is limited by tissue availability, potential immune rejection, and ethical issues (24). Moreover, although neural stem cells from the CNS are potential alternative sources, they have not yet been demonstrated to generate dopaminergic neurons, and are essentially inaccessible without invasive surgery. Similarly, olfballs are an autologous source for transplantation in other neurodegenerative disorders, since they generate other neuronal phenotypes, as well as oligodendrocytes.

Second, these findings demonstrate that a stem/progenitor cell from a peripheral, placodally-derived neural tissue is capable of generating cell types such as oligodendrocytes found only in the central nervous system. In fact, olfballs are similar, in many aspects, to neurospheres, the previously-described EGF-dependent stem cell from the mammalian forebrain (5). There are, however, a number of major differences between olfballs and neurospheres. Although olfballs and neurospheres both readily differentiate into GFAP and GC-positive nonneuronal cells, only olfballs spontaneously generate TH-positive neurons. Moreover, olfballs can be derived in the absence of exogenous EGF, whereas proliferation of neurospheres is dependent upon this growth factor. In spite of these differences, our findings suggest that there may indeed be similar neural stem cell(s) throughout the peripheral and central nervous systems, and that the ultimate developmental outcome for the progeny of these cells is predominantly a function of the local neural environment.

Olfactory epithelial-derived stem cells replace the dopaminergic input in the striatum in the 6-OHDA animal model of Parkinson's disease. The generation of differentiated TH immunopositive neurons from olfactory epithelial-derived stem cells permits these neurons to functionally compensate for, and restore the deficits caused by, the loss of dopaminergic input into the striatum in Parkinson's disease. We show that 1) the TH positive cells which differentiate in culture are dopaminergic neurons ii) the number and neuritic complexity of TH immunopositive cells increase in transplantation experiments iii) the transplanted olfactory epithelial-derived stem cells ameliorates the functional deficit in animal models of Parkinson's disease iv) transplanted adult olfactory epithelial-derived stem cells also differentiate into TH positive neurons. Finally, we transplant human olfactory epithelial derived precursor cells into chemically lesioned rats to obtain TH positive cells and functional recovery.

EXAMPLE 17

Using Neural Stem Cells or Neuronal Progenitor Cells in Autologous Transplants in Treatment of Multiple Sclerosis The olfactory derived precursor cells or cells derived from these precursor cells are implanted into lesion sites of patients having Multiple Sclerosis.

EXAMPLE 18

Isolation of Precursor Cells From Other Peripheral Tissues

We derived precursor cells from the tongue which is another peripheral tissues that contains sensory receptors. The tongue was dissected to remove the epithelial layer that contains the sensory receptors and their underlying basal cells. This layer of tissue is triturated to produce single cells and the single cells are plated in flasks containing DMEM/R12 media supplemented with B-27 (Gibco) and EGF, TGFα, and/or bFGF, as described for the olfactory epithelium. After 2–3 days in a 37 degree Celsius, 5% carbon dioxide tissue culture incubator, most of the cells in the culture are dead or dying. However, a small number of large phase bright cells are present, most of which attach to the flask bottom. Over the next 2 to 6 days these cells divide and produce spherical aggregates that become larger over time and left from the flask surface. The cells in these clusters produce a marker for neural progenitors and stem cells, nestin.

These nestin positive cells can be passaged using the same techniques as used for olfballs. These nestin positive cells can be differentiated into neurons, astrocytes and oligodendrocytes using the same techniques as used for olfballs.

We isolate precursor cells from peripheral tissues containing sensory receptors, other than the olfactory epithelium, using the above techniques. We passage these cells using the same techniques as used for olfballs. We differentiate these cells into neurons, astrocytes and oligodendrocytes using the same techniques as used for olfballs. We induce precursor cells to differentiate by culturing them with growth factors. This is done similarly to the differentiation of precursor cells in example 2.

We grow precursor cells in vitro and differentiate these cells into specific neural cell types. We transfect the olfactory epithelium derived stem cells with the candidate transcription factors including IsI-1, en-1, en-2 and nurr, which have been implicated in regulating motoneuron and striatal phenotypes. With an understanding on how intrinsic and extrinsic factors regulate neural cell fate decisions, it is possible to induce the differentiation of the specific neural cell types required for neuronal transplant therapy.

We modify precursor cells as described above with respect to olfactory epithelial-derived cells using the adenovirus gene transfer system.

We isolate human-derived neural stem cells from peripheral tissues that contain sensory receptors. We use the same procedures as we used to isolate the neural stem cells from the neonate and adult mice. As is known to those skilled in the art, work on primate and human neurospheres with regards to culture conditions provide information on optimizing proliferation of cell spheres and specific cell types. We characterize the growth and differentiation of precursor cells, and their potential for use in transplantation therapy for neurodegenerative diseases.

These precursor cells are useful therapeutically in the treatment of neurodegenerative diseases such as Parkinson's disease and multiple sclerosis. We implant dopamingeric neurons differentiated from precursor cells into the substantia nigra or the striatum of patients having Parkinson's Disease. The olfactory derived precursor cells or cells derived from these precursor cells are implanted into lesion sites of patients having Multiple Sclerosis. We induce precursor cells to differentiate into astrocytes by culturing them with growth factors. This is done similarly to the differentiation of precursor cells in example 2.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Burns S, Chiueh C C, Markey S P, Ebert M H, Jacobowitz D M, Kopin I J (1983) A primate model of parkinsonism: selective destruction of dopaminergic neurons in pars compacta of the substantia nigra by N-methyl-4-phenyl-1,2,3,6-tetra-hydropyridine. Proc Natl Acad Sci (USA) 80:4546–4550
2. Fahn S (1992) Fetal-tissue transplants in Parkinson's disease. New England Journal of Medicine. 3271589–1590
3. Dunnett S B, Annett L E (1991) Nigral transplants in primate models of parkinsonism. In: Lindvall 0, Bjorklund A, Widner H, eds. Intracerebral transplantation in movement disorders. Restorative Neurology 4:27–51
4. Langston J W, Ballard P, Tetrud J W, Irwin 1 (1983) Chronic parkinsonism in humans due to a product of meperidine analog synthesis. Science 219:979–980
5. Remington's Pharmaceutical Sciences, Mack Publishing Company, Easton, Pa., USA
6. Widner H, Tetrud J, Rehncrona S, Snow B, Brundin P, Gustavii B, Bjorklund A, Lindvall P, Langston J W (1993) Bilateral fetal mesencephalic grafting in two patients with parkinsonism induced by 1-methyl-4-phenyl-1,2-3,6-tetrahydropyridine (MPTP). New England Journal of Medicine 327:1556–1563
7. Winkler C, Hammang J P, Bjorklund A (1995) EGF-responsive neural progenitor cells, survive, migrate and differentiate after transplantation into the adult rat striatum. Society for Neuroscience Abstracts 21:2029
8. Gage F H, Coates P W, Palmer T D, Kuhn G, Fisher L J, Suhonen J O, Peterson D A, Suhr S T, Ray J (1995) Survival and differentiation of adult neuronal progenitor cells transplanted to the adult brain. Proc Natl Acad Sci (USA) 92:11870–11883
9. Reynolds B and Weiss S, (1992) Science 255:107
10. Weiss S, Reynolds B, Vescovi A, Morshead C, Craig C, van der Kooy D, (1996) Is there a neural stem cell in the mammalian forebrain? T.I.N.S. 19:9:1
11. Peel A L, Feldman D H, Reier P J (1995) Co-localization of glial and neuronal markers in EGF-generated cultures of pluripotent CNS stem cells. Society for Neuroscience Abstract 21:285
12. Ruth S. Slack, Daniel J. Belliveau, Madelaine Rosenberg, Jasvinder Atwal, Hanns Lochmüller, Raquel Aloyz, Ali Haghighi, B. Lach, Prem Seth, Ellis Cooper, and F. D. Miller (1996) Adenovirus-mediated Gene Transfer of the Tumor Suppressor, p53, Induces Apoptosis in Postmitotic Neurons. The Journal of Cell Biology, Volume 135, No. 4 1085–1096
13. Le Gal La Salle, G., J. J. Roberts, S. Berrard, V. Ridoux, L. D. Stratford-Perricaudet, M. Perricaudet, and J. Mallet, 1993. An adenovirus vector for gene transfer into neurons and glia in the brain, Science (Wash. DC), 259: 988–990.
14. 39. Slack, R. S., and F. D. Miller, 1996. Viral vectors for use in modulating gene expression in neurons, Curr. Opin. Neurobiot, 6:576–583.
15. I. Lefkowitz, H. Waldman, Limiting Dilution Analysis of Cells in the Immune System. Cambridge University Press, Cambridge, U. K. (1979)
16. C. G. Bellows, J. E. Aubin, Dev. Biol. 133, 8 (1989).
17. A. Carlsson, M. Lindqvist, T. Magnusson, Nature 180, 1200 (1957); H. Ehringer, O. Hornykiewicz, Klin. Wschr. 38, 1236 (1960).
18. Female Sprague-Dawley rats or CD 1 albino mice (Charles River, Montreal, Quebec, Canada) weighing 180–200 g or 25–30 g respectively, were anaesthetized with a mixture of ketamine (Ketaset, Ayerst, 90 mg/kg) and xylazine (Rompun, Haver, 10 mg/kg) (intraperitoneal) prior to stereotactic injections of 24 ug of 6-hydroxydopamine hydrobromide (dissolved in 5 ul of 0.9% saline containing 0.2 mg/ml ascorbate) into the right medial forebrain bundle (Tooth bar:-2.4 mm; A:-4.4 mm; L:1.0 mm; V:7.5 mm (19)). Two weeks after the lesion, animals were tested for rotational behavior as previously described (20). Animals were immunosuppressed with cyclosporine (Sandimmune, Sandoz, 40 mg/kg, intraperitoneal) once a day and the immunosuppression was continued until the day of sacrifice. For olfball transplantation, anaesthetized animals were mounted in a Kopf stereotactic apparatus, and 2×2.5 $\mu$l aliquots of olfballs were injected unilaterally into the lesioned caudate putamen or bilaterally in some animals. The injections were made using a 5 ul Hamilton syringe at the following coordinates: Tooth bar, −2.4 mm; A: 0.2; L: 3.0; V:

5.5–6.0 (19). Injections were performed over a period of 3 minutes, a further 5 minutes was allowed for diffusion, and the needle was then retracted. These 5 µl injections contained olfballs derived from one neonatal pup cultured for 7–14 days. For the BrdU experiments, BrdU (10 µM) was added to culture media for 18 hours, after which the olfballs were washed three times with fresh media to remove the BrdU, and then the olfballs tranplanted one day later. Sixteen days following transplantation, animals were anaesthetized with an overdose of i.p. pentobarbital, and perfused transcardially sequentially with saline and 4% paraformaldehyde in phosphate buffer (PB, 0.1M, pH 7.4). The brains were post-fixed for 18 hours at 4° C., and then cryoprotected for 48 hours in 30% sucrose dissolved in PB. Brains were sectioned on a freezing microtome in the coronal plane at 40 um. Free-floating sections were collected in phosphate buffered saline (0.1M, PBS) and processed for TH, β-galactosidase (Boehringer Mannheim), GFAP, or nestin immunocytochemistry. Sections were initially incubated in a PBS solution containing 0.5% sodium borohydride for 20 minutes, rapidly washed six times, and then incubated in PBS containing 5% BSA. Sections were then incubated in a PBS solution containing 0.1% Triton X-100, 2% BSA and either anti-TH (1:1500), or monoclonal β-galactosidase (1:500) or anti-nestin antibody (1:1000). After overnight incubation in the primary antibodies at 4° C., sections were rinsed in PBS (3×, 5 mins per wash), and incubated for 1 hour at room temperature in PBS containing biotinylated goat anti-rabbit IgG (1:200, Vector Laboratories), 0.1% Triton X-100, and 2% BSA. After 3 brief washes in PBS, sections were incubated for 1 hour at room temperature in PBS containing an avidin-biotin complex (ABC, Vector Laboratories). Following 3 washes in PBS, the immunohistochemical reaction product was revealed by incubation in Tris buffer (0.05M, pH 7.6) containing diaminobenzidine tetrahydrochloride (DAB, Sigma) (0.025 g/100 ml), 1% 1M imidazole, and 0.3% hydrogen peroxide. Sections were exposed to DAB for 15 minutes, rinsed 6× in PBS, mounted onto chrom-alum coated slides, air dried, dehydrated in graded alcohols, and coverslipped with Permount.

19. G. Paxinos and C. Watson, The Rat Brain in Stereotaxic Coordinates. Academic Press, San Diego 1986.

20. U. Ungerstedt and G. W. Arbuthnott, Brain Res. 24, 485 (1970).

21. A. Gloster, W. Wu, A. Speellman, S. Weiss, C. Causing, C. Pozniak, B. Reynolds, E. Chang, J. G. Toma, F. D. Miller, J. Neurosci. 14, 7319 (1994); S. Bamji, F. D. Miller, J. Comp. Neurol. 374, 52 (1996).

22. BrdU immunohistochemistry was performed as described (23), with some modifications. Following pre-incubation (23), free-floating sections were incubated for 16 hours in PBS containing anti-BrdU (1:40, Becton-Dickinson, San Jose, Calif.) and 2% BSA at 4 C. Following 3 brief washes in PBS, sections were incubated for 1 h in PBS containing secondary antibody (biotinylated anti-mouse IgG, 1:200, 1:200, Vector, Burlinghame, Calif.) and 2% BSA. Sections were rinsed in PBS (3×5 min), incubated in avidin-biotin complex (ABC, 1%, in PBS, Vector, Burlinghame, Calif.) for 1 hour, again rinsed in PBS (3×5 min), and the immunohistochemical reaction product revealed by incubating the sections for 7–10 minutes in a solution containing 0.37 gm nickel ammonium sulfate, 25 mg DAB, and 2 ul of 30% hydrogen peroxide dissolved in 100 ml of Tris buffer (0.05 M, pH 7.6), yielding a blue-black reaction product. Sections were then thoroughly rinsed in PBS, and prepared for immunohistochemistry for the second antigen (18).

23. E. Soriano, J. A. Del Rio, J. Histochem. Cytochem. 39, 255 (1991).

24. S. Fahn, New England J. Med. 327, 1589 (1992).

We claim:

1. A composition consisting of an isolated population of neural stem cells of a postnatal mammal and a carrier, wherein said neural stem cells form non-adherent clusters in culture, are self renewing, proliferate in an EGF-independent manner, express nestin, and differentiate, in the presence of serum, into neurons expressing tyrosine hydroxylase, said stem cells produced by a method comprising the steps of:
    (a) providing a culture of peripheral tissue containing sensory receptors from said mammal;
    (b) isolating neural stem cells from said peripheral tissue, based on the tendency of said neural stem cells to aggregate and form non-adherent clusters in culture, wherein said neural stem cells form non-adherent clusters in culture, are self renewing, proliferate in an EGF-independent manner, express nestin, and differentiate, in the presence of serum, into neurons expressing tyrosine hydroxylase.

2. A composition consisting of an isolated population of neural stem cells of a postnatal mammal and a carrier, wherein said neural stem cells form non-adherent clusters in culture, are self renewing, proliferate in an EGF-independent manner, express nestin, and differentiate, in the presence of serum, into neurons expressing tyrosine hydroxylase.

3. The composition of claim 1, wherein said peripheral tissue comprises olfactory epithelium.

4. The composition of claim 1, wherein said peripheral tissue comprises tongue.

5. The composition of claim 1, wherein said neural stem cells are transfected with a heterologous gene.

6. The composition of claim 5, wherein said gene encodes a trophic factor.

7. The composition of claim 1, wherein said neural stem cells are human stem cells.

8. The composition of claim 1, formulated in a pharmaceutically acceptable carrier, auxiliary or excipient.

9. The composition of claim 2, formulated in a pharmaceutically acceptable carrier, auxiliary or excipient.

10. The composition of claim 2, wherein said neural stem cells are human stem cells.

11. The composition of claim 2, formulated in a pharmaceutically acceptable carrier, auxiliary or excipient.

* * * * *

UNITED STATES PATENT AND TRADEMARK OFFICE
CERTIFICATE OF CORRECTION

PATENT NO. : 6,969,608 B1
APPLICATION NO. : 08/920272
DATED : November 29, 2005
INVENTOR(S) : Miller et al.

It is certified that error appears in the above-identified patent and that said Letters Patent is hereby corrected as shown below:

Column 5, Line 59, replace "oligodedrocytes" with
--oligodendrocytes--.

Column 7, Line 9, replace "astroycytes" with --astrocytes--.

Column 8,
Line 2, replace "50/u" with --50 $\mu$m--; and
Line 32, replace "nestin" with --Nestin--.

Column 9, Line 8, replace "juvenile" with --(juvenile--.

Column 10,
Line 24, replace "tongue" with --tongue.--; and
Line 45, replace "teezed" with --tweezed--.

Column 11, Line 62, replace "florescence" with --fluorescence--.

Column 12, Line 1, replace "(Nation" with --National--.

Column 15,
Line 32, replace "stiatal" with --striatal--;
Line 44, replace "dendrocyytes" with --dendrocytes--;
Line 54, replace "provide." with --provide much information on the role of the local environment in determining cell fate. --; and
Line 59ff., replace "Epithelium Much Information on the Role of the Local Environment in Determining Cell Fate" with --Epithelium--.

Column 17, Line 24, replace "oligodendocytes" with
--oligodendrocytes--.

Column 18, Line 65, replace "patients" with --patient's--.

Column 20,
Line 62, replace "Ta1:nlacZ" with --T$\alpha$1:nlacZ--;
Line 63, replace "Ta1" with --T$\alpha$1--; and
Line 64, replace "a-tubulin" with --$\alpha$-tubulin--.

UNITED STATES PATENT AND TRADEMARK OFFICE
CERTIFICATE OF CORRECTION

PATENT NO. : 6,969,608 B1
APPLICATION NO. : 08/920272
DATED : November 29, 2005
INVENTOR(S) : Miller et al.

It is certified that error appears in the above-identified patent and that said Letters Patent is hereby corrected as shown below:

Column 22, Line 47, replace "disoxide" with --dioxide--.

Column 24,
    Line 2, replace "USA" with --USA 1985--; and
    Line 37, replace "14.   39." with --14. --.

Signed and Sealed this

Nineteenth Day of December, 2006

JON W. DUDAS
*Director of the United States Patent and Trademark Office*